(12) United States Patent
Neijzen et al.

(10) Patent No.: US 9,983,128 B2
(45) Date of Patent: May 29, 2018

(54) PARALLEL OPTICAL EXAMINATIONS OF A SAMPLE

(71) Applicant: KONINKLIJKE PHILIPS N.V., Eindhoven (NL)

(72) Inventors: Jacobus Hermanus Maria Neijzen, Heeze (NL); Wendy Uyen Dittmer, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 440 days.

(21) Appl. No.: 14/355,462

(22) PCT Filed: Oct. 29, 2012

(86) PCT No.: PCT/IB2012/055973
§ 371 (c)(1),
(2) Date: Apr. 30, 2014

(87) PCT Pub. No.: WO2013/064961
PCT Pub. Date: May 10, 2013

(65) Prior Publication Data
US 2014/0286826 A1  Sep. 25, 2014

Related U.S. Application Data

(60) Provisional application No. 61/555,025, filed on Nov. 3, 2011.

(51) Int. Cl.
*G01N 21/55* (2014.01)
*G01N 21/03* (2006.01)
(Continued)

(52) U.S. Cl.
CPC ........ *G01N 21/55* (2013.01); *B01L 3/502715* (2013.01); *G01N 21/0303* (2013.01);
(Continued)

(58) Field of Classification Search
None
See application file for complete search history.

(56) References Cited

U.S. PATENT DOCUMENTS 4,608,344 A  8/1986 Carter
5,082,629 A  1/1992 Burgess
(Continued)

FOREIGN PATENT DOCUMENTS

WO  2008155716 A1  12/2008

*Primary Examiner* — Samuel P Siefke (57) ABSTRACT

A first output light beam (L2) that originates from a total internal reflection at a detection surface (111) of a total internal reflection TIR chamber (110) and a second output light beam (L2') that comes from the interior of an inspectable chamber (120, 220, 320, 420, 520, 620) are both received within an observation region (OR). Preferably, these output light beams are detected with the same light detector, e.g. an image sensor (12). A total internal reflection at the TIR chamber and reflected light from inside the inspectable chamber are both directed to the same observation region (OR). This is for example enabled by different inclinations of the windows encountered by the first and the second output light beams, by different optical elements (407) in the paths of the output light beams, and/or by light scattering surface structures (122, 223, 322, 422, 522, 622) in the inspectable chamber.

6 Claims, 4 Drawing Sheets (51) Int. Cl.

| | | |
|---|---|---|
| *G01N 21/25* | (2006.01) | |
| *G01N 21/552* | (2014.01) | |
| *G01N 21/78* | (2006.01) | |
| *G01N 33/543* | (2006.01) | |
| *B01L 3/00* | (2006.01) | |
| *G01N 21/64* | (2006.01) | |
| *G01N 21/84* | (2006.01) | |

(52) U.S. Cl.
CPC ......... *G01N 21/253* (2013.01); *G01N 21/552* (2013.01); *G01N 21/78* (2013.01); *G01N 33/54373* (2013.01); *B01L 2300/0654* (2013.01); *B01L 2300/0816* (2013.01); *B01L 2300/0864* (2013.01); *B01L 2300/168* (2013.01); *B01L 2400/0688* (2013.01); *G01N 21/648* (2013.01); *G01N 21/8483* (2013.01); *G01N 33/54326* (2013.01); *G01N 2021/0325* (2013.01); *G01N 2021/0328* (2013.01); *G01N 2021/6482* (2013.01)

(56) References Cited

U.S. PATENT DOCUMENTS

| | | |
|---|---|---|
| 5,096,669 A | 3/1992 | Lauks et al. |
| 5,211,914 A | 5/1993 | Vogel et al. |
| 6,867,869 B2 | 3/2005 | Budach et al. |
| 2003/0175160 A1 | 9/2003 | Archibald et al. |
| 2004/0169863 A1 | 9/2004 | Kawate |
| 2005/0175273 A1 | 8/2005 | Iida |
| 2007/0031283 A1 | 2/2007 | Davis et al. |
| 2008/0153096 A1 | 6/2008 | Witty et al. |
| 2010/0310423 A1 | 12/2010 | Nieuwenhuis |
| 2011/0188030 A1 | 8/2011 | Vershuren et al. |
| 2011/0201099 A1 | 8/2011 | Anderson et al. |

PARALLEL OPTICAL EXAMINATIONS OF A SAMPLE

CROSS-REFERENCE TO PRIOR APPLICATIONS

This application is the U.S. National Phase application under 35 U.S.C. § 371 of International Application No. PCT/IB2012/055973, filed on Oct. 29, 2012, which claims the benefit of U.S. Provisional Patent Application No. 61/555,025, filed on Nov. 3, 2011. These applications are hereby incorporated by reference herein.

FIELD OF THE INVENTION

The invention relates to a cartridge, a sensor apparatus, and a method for the optical examination of a sample, said examination comprising the total internal reflection of a light beam at a detection surface.

BACKGROUND OF THE INVENTION

The US 2010/0310423 A1 discloses a biosensor cartridge having a well with a sensor surface at which sample particles can be detected by Frustrated Total Internal Reflection (FTIR) of a light beam. In an alternative embodiment, the sensor surface may have a jagged surface structure by which light is directed for a short distance through the sample. With the described biosensor cartridge, a sample can be examined in a region close to the sensor surface.

SUMMARY OF THE INVENTION

It is an object of the invention to provide means that allow for a more versatile and/or fast examination of a sample, particularly for the determination of clinical parameters of a biological sample.

According to a first aspect a cartridge is provided for the optical examination of a sample, for example of a biological body fluid like blood, saliva or urine. The term "cartridge" shall denote an exchangeable element or unit with which a sample can be provided to a sensor apparatus for processing. The cartridge will usually be a disposable component which is used only once for a single sample. The cartridge includes the following components:

a) A first sample chamber with a detection surface. The term "sample chamber" shall denote a typically empty cavity or a cavity filled with some substance like a gel that may absorb a sample substance; it may be an open cavity, a closed cavity, or a cavity connected to other cavities by fluid connection channels. Due to the functionality explained below, the first sample chamber will in the following be called "TIR chamber" for purposes of reference.

b) A second sample chamber that will in the following be called "inspectable chamber" for purposes of reference. The inspectable chamber and the TIR chamber will typically be separated (disconnected), though it is also comprised by the invention that they are just different parts of one superordinated chamber.

Moreover, there shall be an observation region adjacent to the cartridge in which a first output light beam, which originates from a total internal reflection at the mentioned detection surface, and a second output light beam, which comes from the interior of the inspectable chamber, can be received (or "be seen").

The aforementioned "observation region" typically refers to a two-dimensional (piece of) surface, area, or zone that has some geometrical relation to the cartridge but that typically does not correspond to a tangible component. It will usually be planar and lie outside the material of the cartridge or at most on the (outer) surface of said material. As will be explained in more detail with respect to preferred embodiments of the invention, a lens may be located in or at the observation region to capture the first and second output light beams. It should be noted, however, that the first and second output light beams will typically be received at different sub-regions of the observation region.

When reference is made to a total internal reflection taking place at the detection surface, the (sample-) material filling the TIR chamber is assumed to have a refractive index n between about 1.1 and 1.6, preferably of about 1.3 (i.e. the refractive index of water).

According to a second aspect, a sensor apparatus for the optical examination of the sample includes the following components:

a) A first sample chamber, called "TIR chamber" in the following, with a detection surface.

b) A second sample chamber, called "inspectable chamber" in the following.

c) At least one light detector that is arranged at an observation region to receive a first output light beam, which originates from a total internal reflection at the detection surface, and a second output light beam, which comes from the interior of the inspectable chamber.

According to a third aspect, a method for the optical examination of a sample includes the following steps:

a) Filling sample into a first sample chamber ("TIR chamber") with a detection surface and into a second sample chamber ("inspectable chamber").

b) Directing an input light beam to the detection surface such that it is totally internally reflected into a first output light beam which passes through an observation region.

c) Generating a second output light beam inside the inspectable chamber that leaves said chamber and also passes through the observation region.

d) Detecting the first output light beam and the second output light beam after their passage through the observation region.

The cartridge, the sensor apparatus, and the method described above comprise the same feature that an observation region can be identified from which total internal reflection at a detection surface of a TIR chamber can be seen simultaneously with light coming from the interior of an inspectable sample chamber. Accordingly, different optical examinations can be made in said two sample chambers that can in parallel be observed at the observation region. This reduces the time necessary to obtain a plurality of examination results, which is particularly important in clinical applications. Moreover, the different optical examinations can be made in basically the same apparatus that is used (or has previously been used) for the execution of just one type of optical examination.

As the cartridge, the sensor apparatus, and the method are related embodiments of the invention, explanations and definitions provided for one of them are analogously valid for the other embodiments, too. Moreover, the sensor apparatus may particularly comprise the described cartridge, and the method may particularly be executed with the described cartridge and/or the described sensor apparatus. In the following, various preferred embodiments of the invention will be described that relate equally to the cartridge, the sensor apparatus and the method defined above.

The inspectable chamber allows for an optical examination of a sample in its interior (i.e. not only close to a surface of the chamber). As an example of clinical importance, the inspectable chamber may comprise a colorimetric assay. In a colorimetric assay, a color change of reagents serves as an indicator of sample parameters of interest, for example the concentration of electrolytes. To evaluate a colorimetric assay, light generated or affected by reagents within the interior of the inspectable chamber must be detected. This is possible by the detection of the second output light beam that comes from the interior of the inspectable chamber.

The second output light beam may in general comprise light generated by any suitable process within the inspectable chamber, for example by fluorescence. In a preferred embodiment, the second output light beam comprises light that was reflected inside the inspectable chamber. This may particularly comprise a reflection by reagents of a colorimetric assay, wherein the reflection changes the spectral composition of the reflected light in a characteristic way.

In general, the first output light beam and the second output light beam may be detected by different light detectors arranged at appropriate positions at the observation region. In a preferred embodiment, the first and second output light beam are however detected with the same light detector. Using one and the same detector for both output light beams has the advantage that hardware costs, space consumption, and maintenance effort are minimized. Even with a single light detector, a distinction between detector signals resulting from the first or the second output light beam can readily be achieved. For example, the corresponding input light beams may be modulated in characteristic manners, or they may have different spectra.

At least one of the light detectors that is used to detect the first and/or the second output light beam may comprise an image sensor. With an image sensor, processes in an extended area can be observed simultaneously. An image sensor may particularly be used in combination with the aforementioned embodiment, i.e. as a single light detector for both the first and the second output light beam. In this case the two output light beams may be mapped onto different regions of the image plane, yielding a spatial separation of the contributions of the first and the second output light beam.

The second output light beam leaves the inspectable chamber through a surface that will in the following be called "inspection surface" for the purpose of reference. The inspection surface will typically be a planar part (facet) of the whole interior surface of the inspectable chamber.

According to one preferred embodiment, the aforementioned inspection surface of the inspectable chamber is parallel to the detection surface of the TIR chamber. Additionally, both surfaces may optionally lie in the same plane. When the inspection surface and the detection surface are parallel, this simplifies the layout of the component (cartridge) housing the TIR chamber and the inspectable chamber because both sample chambers can substantially have the same design.

According to another embodiment, the inspection surface of the inspectable chamber has a light scattering surface structure. Such a surface structure may for example be realized by a plurality of protrusions that refract incident light into different directions (into or out of the inspectable chamber). The light scattering surface structure may particularly be used when the inspection surface is parallel to the detection surface because it allows for illuminating both surfaces from the same direction. This is because the illumination is not totally internally reflected at the inspection surface (as it is at the parallel detection surface) due to the light scattering structure.

The aforementioned light scattering surface structure may preferably comprise reagents, for example reagents that are needed for a colorimetric assay. The material in which the inspectable chamber is realized (e.g. glass or transparent plastic) may then actually have a planar surface on which the reagents are deposited such that, optically, a light scattering surface structure results.

In terms of costs and design simplicity, it would be favorable to use a similar or identical design for the TIR chamber and the inspectable chamber. This approach is however in conflict with the requirement that both chambers shall be observed from the same observation region, one chamber under an angle of total internal reflection, the other not.

In order to deal with the aforementioned dilemma, at least one optical element may be provided for redirecting the second output light beam, i.e. to deflect it on its path from the inspectable chamber to the observation region. Due to the redirection of the second output light beam, it is possible to use the same design for the TIR chamber and the inspectable chamber. It should be noted that equivalently an optical element can be provided that redirects the first output light beam such that both the first and the second output light beams reach the observation region. Redirecting the second output light beam just has the advantage that it can be added to many existing sensor devices, which have been designed for total internal reflection only.

The mentioned optical element may particularly comprise a cavity through which the second output light beam and/or an input light beam passes. Said cavity is typically formed in the (cartridge-) material which houses the inspectable chamber. Moreover, a "passage through the cavity" shall typically comprise that the second output light beam enters the cavity through one surface thereof and leaves it through another surface thereof. Realizing the optical element by a cavity has the advantage that it can readily be produced, for example by just leaving out some material during the production of an injection molded cartridge.

In another embodiment of the invention, the first output light beam and the second output light beam leave the material in which the TIR chamber and the inspectable chamber are provided through exit windows of different inclination. Typically, the mentioned material will be the same material for both sample chambers (i.e. both sample chambers are realized in the same body) and/or be the material of a disposable cartridge. Moreover, the term "exit window" shall in this embodiment preferably refer to a "final exit window", which means that the corresponding output light beam encounters no other component between said exit window and the observation region. Due to the different inclinations of the exit windows, the first and the second output light beam are differently refracted when they leave the material. This can be used to guide both beams towards the same observation region.

According to another embodiment of the invention, the inspection surface of the inspectable chamber is not parallel to the detection surface of the TIR chamber. This allows for an arrangement of the inspection surface at an angle other than an angle of total internal reflection (seen from the observation region), which avoids the associated dilemma described above for parallel surfaces.

The detection surface and the inspectable chamber may be illuminated with input light beams that are parallel to each other. This has the advantage that a single light source can be used for the illumination.

A problem of the aforementioned approach is however that the parallel input light beams must be totally internally reflected at the TIR chamber and enter the inspectable chamber, respectively. These are again conflicting requirements (as discussed above with respect to the output side) which usually prohibit to use the same design for the both sample chambers. According to another embodiment of the invention, the detection surface and the inspectable chamber are therefore illuminated with input light beams that are not parallel to each other. In this case the described problems can be solved by directing the input light beams onto the corresponding surfaces under angles below and above the critical angle of total internal reflection, respectively.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Embodiments of the present invention will in the following be described with respect to biosensors for the detection of specific target molecules in body fluids like saliva, urine, or blood. A biosensor platform as it is for example known from the US 2010/0310423 A1 (also called Philips "Magnotech" platform) uses magnetic particles in an immunoassay to detect protein and employs an optical detection method called FTIR (Frustrated Total Internal Reflection). It is desirable to extend the standard application range of such a biosensor in the direction of clinical chemistry parameters by enabling the measurement of other analytes (electrolytes, metabolites, small molecules) in the same multi-chamber cartridge that is used for immunoassay detection of proteins.

To put it differently, the aim is to realize simultaneously immunoassay based detection as well as colorimetric detection of clinical chemistry parameters in a rapid, compact analyzer that uses a small volume of blood. The advantage of being able to perform both detection of proteins and electrolytes/substrates is demonstrated by examples in which the status of a patient is guided by several parameters (e.g. chronic heart failure).

In the mentioned biosensors, the immunoassay detection system is optimized for FTIR detection in order to achieve the high sensitivity required for the measurements of low concentrations of proteins in blood. In order to maintain the immunoassay performance, it is highly desirable that the main adaptation for detection of clinical chemistry parameters comes from the cartridge. It has to be realized within the form factor of the available (e.g. Magnotech) cartridge and in such a way that the standard detection branch of the analyzer can be used for detection of both FTIR and colorimetric signals. This is because changes in the detection branch are extremely difficult without disturbing the existing FTIR detection for the immunoassay application. It is however possible to alter the illumination branch, because a change (or addition) in the illumination branch eventually has less impact on the analyzer for FTIR than a change of the detection branch.

Furthermore, it is also desirable to be able to use existing reagent technology for the generation of a colorimetric signal in clinical chemistry detection. A colorimetric signal generated in a solution may for example be detected using optical absorption. However, the following examples will rather describe a cartridge that enables detection using reflectance. Reflectance has the advantage that it can be applied to lateral flow strips (based e.g. on nitrocellulose paper or plastic). Deposition and stabilization of reagents for optimal assay performance is well known in the art (U.S. Pat. No. 5,211,914).

Reflectance may be measured by the reflected light from the sample relative to a standard. As known procedures of reflectance measurement have various drawbacks and/or cannot readily be integrated into an FTIR sensor, the present invention tries to
- adapt the illumination branch of an FTIR analyzer;
- modify the existing cartridge for both FTIR and reflectance;
- not change the existing FTIR detection branch.

In this way the performance of FTIR is maintained, small sample volumes/parameter are enabled, and the small form factor for both analyzer and cartridge is maintained.

Accordingly, an essential part is to change a cartridge in such a way that the angle of incidence on the bottom of the (colorimetric) detection chamber becomes smaller that the critical angle for reflection, so that it becomes possible to look into said detection chamber. It prevents that the bottom of the detection chamber from acting like a mirror which prevents light from the inside of the detection chamber reaching the detector.

The proposed solution can be realized by various options, for example
- by a scattering bottom of the detection chamber or a scattering layer on the bottom;
- by a local removal of the usual cartridge window;
- by an indentation in the cartridge bottom (acting as prism redirecting the output beam);
- by a detection through a side wall of detection chamber.

All these options can be applied to a cartridge locally such that only chambers intended for reflectance detection are affected, while maintaining the FTIR chambers as is. In the following, embodiments of these options will be described in more detail.

Figure 1:
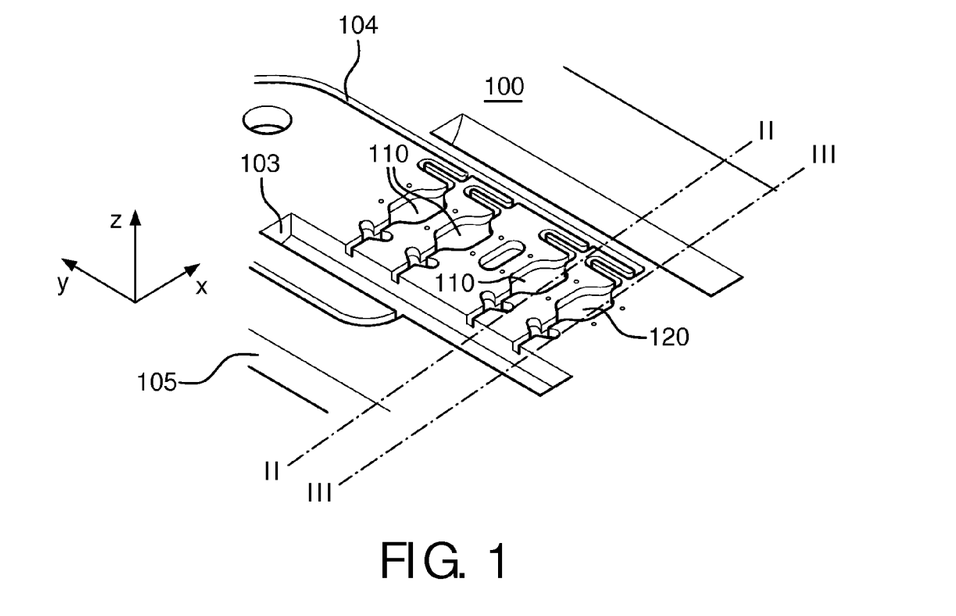
FIG. 1 shows in a perspective view the top side of a first cartridge according to the present invention in which three TIR chambers and one inspectable chamber are provided.
Figure 2:
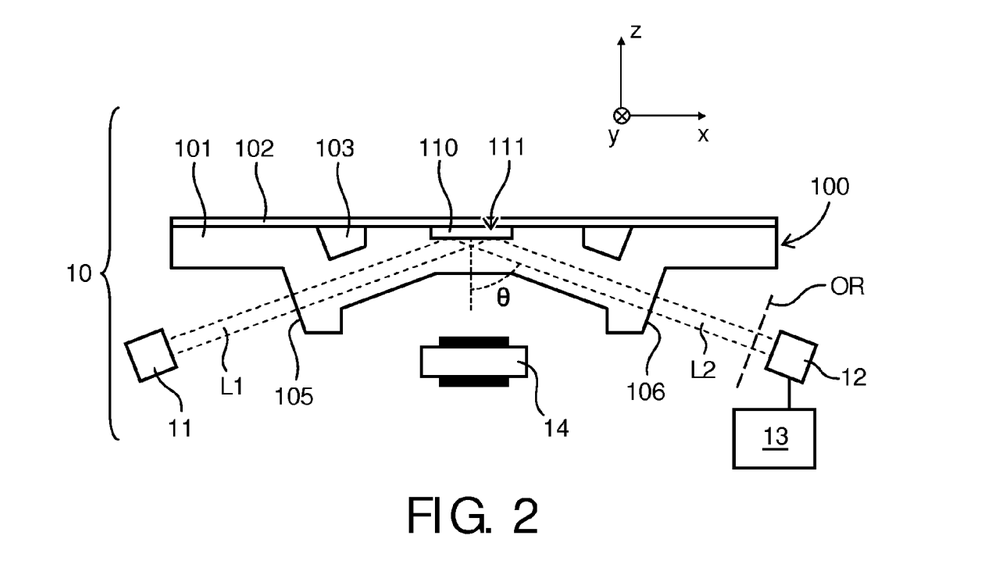
FIG. 2 shows a cross section along line II-II of FIG. 1 through a TIR chamber and an associated sensor apparatus.
Figure 3:
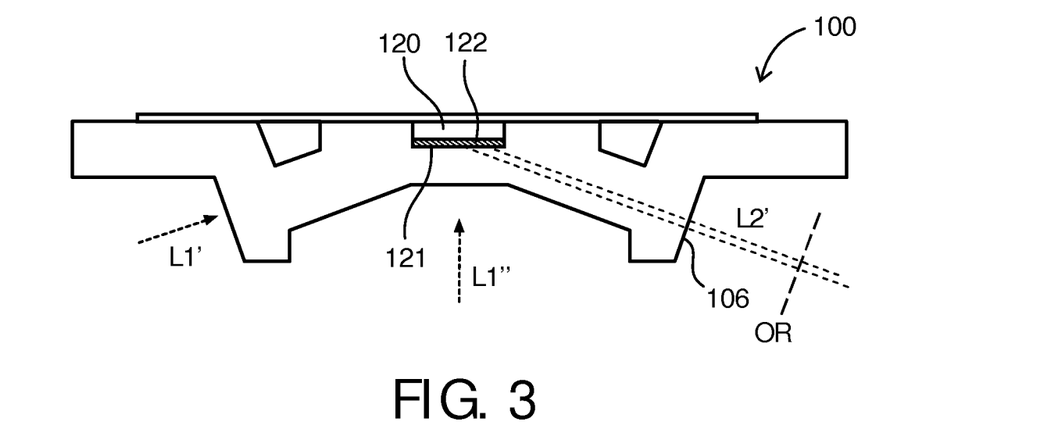
FIG. 3 shows a cross section along line III-III of FIG. 1 through an inspectable chamber.

FIGS. 1, 2, and 3 refer to a first embodiment of the invention. FIG. 1 shows a perspective top view onto the associated cartridge 100 (with removed cover foil 102). The cartridge 100 comprises four first wells or sample chambers 110, 120, and one central chamber. The central chamber serves as a "true white reference" chamber which is not filled with a sample and is hence not connected to any fluidic channels. The other four chambers 110 and 120 are identical in design and arranged one behind the other in y-direction. The leftmost three of these chambers will be called "TIR chambers" 110 in the following. The rightmost one of these chambers will be called "inspectable chamber" 120 in the following.

Additional components that can be seen in FIG. 1 comprise channels 104 for the supply of sample fluid to the sample chambers 110, 120, a reservoir 103 for excess sample, and a lateral light entrance window 105.

FIG. 2 shows a section through the cartridge 100 along line II-II of FIG. 1, said cross section passing through a TIR chamber 110. In addition to FIG. 1, the drawing also shows a planar cover foil 102 that covers and seals the body 101 of the cartridge 100 on the top side.

Moreover, FIG. 2 schematically depicts components of an analyzer that constitutes, together with the cartridge 100, a sensor apparatus 10 and with which optical examinations can be made within the cartridge 100. As the analyzer substantially stays the same, it is not shown in the residual Figures.

The cartridge 100 may for example be made from glass or transparent plastic like poly-styrene. In its TIR chamber 110, a sample fluid with target components to be detected (e.g. drugs, antibodies, DNA, parathyroid hormone PTH etc.) can be provided. The sample will typically also comprise magnetic particles, for example superparamagnetic beads, wherein these particles may be bound as labels to the aforementioned target components. It should be noted that instead of magnetic particles other label particles, for example electrically charged or fluorescent particles, could be used as well.

A "detection surface" 111 forms the bottom side of the TIR chamber 110. One or more "detection spots" may be disposed on this detection surface 111 which comprise binding sites, e.g. antibodies, which can specifically bind the target components.

The sensor device 10 further comprises a light source 11 for emitting a (first) "input light beam" L1 that enters the cartridge 100 through a tilted entrance window 105 and arrives at the detection surface 111 at an angle θ larger than the critical angle of total internal reflection (TIR). It is therefore totally internally reflected as a (first) "output light beam" L2 which leaves the cartridge 100 through a tilted exit window 106 and is detected by a light detector, e.g. by the light-sensitive pixels of a camera 12 that is arranged in an observation region OR. The light detector 12 thus generates an image of the detection surface, which is further processed in the evaluation unit 13 (e.g. a microprocessor).

The sensor device 10 further comprises a magnetic field generator, for example comprising electromagnets 14 with a coil and a core disposed at the bottom and/or at the top (not shown) of the cartridge, for controllably generating a magnetic field at the detection surface 111 and in the adjacent space of the TIR chamber 110. With the help of this magnetic field, magnetic particles can be manipulated, i.e. be magnetized and particularly be moved (if magnetic fields with gradients are used). Thus it is for example possible to attract magnetic particles to the detection surface 111 in order to accelerate the binding of the associated target component to said surface.

The described sensor apparatus 10 applies optical means for the detection of magnetic particles in the TIR chamber 110. For eliminating or at least minimizing the influence of background (e.g. of the sample fluid, such as saliva, blood, etc.), the detection technique is surface-specific. This is achieved by using the principle of Frustrated Total Internal Reflection. This principle is based on the fact that an evanescent wave propagates (exponentially dropping) into the TIR chamber 110 when the incident light beam L1 is totally internally reflected. If this evanescent wave then interacts with another medium having a different refractive index from water like the magnetic particles, part of the input light will be coupled into the sample fluid (this is called "frustrated total internal reflection"), and the reflected intensity will be reduced (while the reflected intensity will be 100% for a clean interface and no interaction). Further details of this procedure may be found in the WO 2008/072156 A2, which is incorporated into the present text by reference.

FIG. 3 shows a section along line III-III of FIG. 1, said section passing through the inspectable chamber 120. It can be seen that this inspectable chamber 120 is in shape and size substantially identical to the TIR chamber 110. It comprises at its bottom an "inspection surface" 121 through which a second output light beam L2' leaves the interior of the inspectable chamber 120. As the second output light beam L2' is parallel to the first output light beam L2 and encounters the same geometry of components on its way out of the cartridge 100, leaving the latter through an exit window 106, the second output light beam L2' also reaches the observation region OR. Accordingly, it can be detected with the same light detector 12 as the first output light beam L2 (which is not shown again in FIG. 3).

The problem with the described design is that the inspection surface 121 is seen under an angle of total internal reflection from the observation region OR. This would actually prevent that light from inside the inspectable chamber 120 can reach the observation region OR on the described path. In order to solve this issue, a light scattering structure is provided in real optical contact to the inspection surface 121. This allows light from the interior of the inspectable chamber 120 to leave through this surface in the direction of the observation region OR. In the cartridge 100, said surface structure is provided by the color changing reagents 122 of the colorimetric assay which are deposited directly on the (planar) inspection surface 121. The light scattering properties of the reagents 122 enable the outcoupling of light into the second output light beam L2'.

The reagents 122 may for example be adapted for the (qualitative or quantitative) detection of a wide range of analytes including potassium, sodium, creatinine, alkaline phosphatase, amylase, cholesterol, creatinine kinase, creatinine, glucose, GOT, GPT, HDL, Hb, K+, pancreatic amylase, triglycerides, uric acid, urea.

Moreover, the reagents 122 enable the incoupling of a second input light beam L1' that is directed towards the inspection surface 121. The second input light beam L1' is parallel to the first input light beam L1 (FIG. 2) and may preferably be generated by the same light source 11. The light of the second input light beam L1' is not totally internally reflected at the inspection surface 121 because it is scattered into the inspectable chamber 120 by the reagents 122.

FIG. 3 also indicates the possibility to illuminate the inspectable chamber 120 from a direction that is not parallel to the first input light beam, for example with a (third) input light beam L1" from below (or, not shown, from above), particularly from a direction perpendicular to the inspection surface 121.

The described first embodiment provides a simple and effective solution under the conditions that the color change takes place in a single layer (like in a potassium strip) and that this layer can properly deposited on the inspection surface 121. In practice, these conditions are not always met. A preferred alternative embodiment is therefore to attach the color changing layer with the reagents to the top foil covering the cartridge. This approach is used in the following embodiments to be described. As the design of the TIR chamber and the analyzer remain substantially the same, they will not be described again for the following embodiments.

Figure 4:
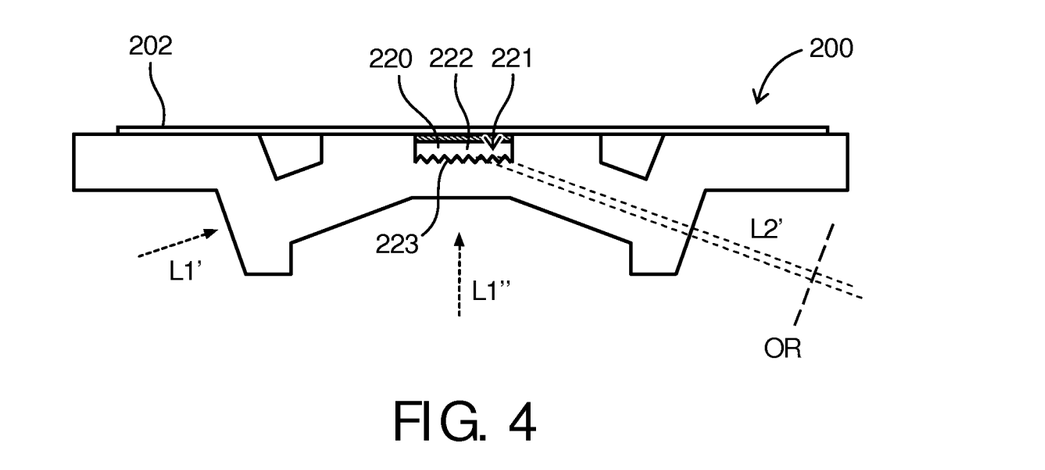
FIG. 4 shows a cross section through the inspectable chamber of a cartridge with an inspection surface having a light scattering surface structure.

FIG. 4 shows a section (analogous to that of FIG. 3) through the inspectable chamber 220 of a second embodiment of a cartridge 200. Components that are similar or identical to those of the previous embodiment have corresponding reference signs, increased by 100, and are not described again. As already mentioned above, the reagents 222 are now provided on the top surface of the inspectable chamber 220, i.e. attached to the cover foil 202. Moreover, the inspection surface 221 itself has a light scattering surface structure, comprising for example specific triangular structures or wedges 223 similar to those described in the US 2010/0310423 A1. Such a design has successfully been tested using pyramid structures with a top angle of about 145° and about 90°.

Illumination of the inspectable chamber 220 may be achieved by input light beams L1', L1" as described above with respect to FIG. 3.

Figure 5:
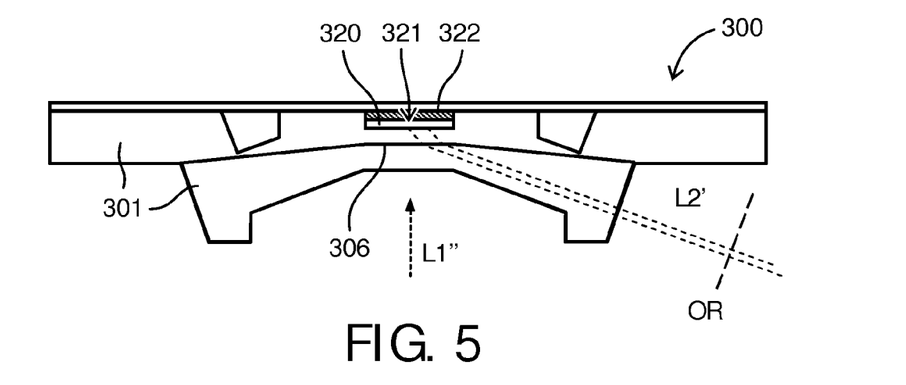
FIG. 5 shows a cross section through the inspectable chamber of a cartridge with a cartridge exit window of modified inclination.

FIG. 5 shows a section through the inspectable chamber 320 of a third cartridge 300, wherein the reagents 322 are again provided on the top surface of the inspectable chamber 320. The inspection surface 321 at the bottom of the inspectable chamber 320 is planar and parallel to (optionally even in the same plane as) the detection surface of the corresponding TIR chamber (FIG. 2).

A (second) output light beam L2' can leave the inspectable chamber 320 only under angles smaller than the critical angle of total internal reflection. Therefore this light cannot reach the observation region OR on a similar path as the totally internally reflected first output light beam L2 (FIG. 2). To let the second output light beam L2' nevertheless reach the observation region OR, the exit window 306 through which this light beam leaves the cartridge 300 is oriented at a suitable inclination (different from the inclination of the exit window 106 in FIG. 2).

Figure 6:
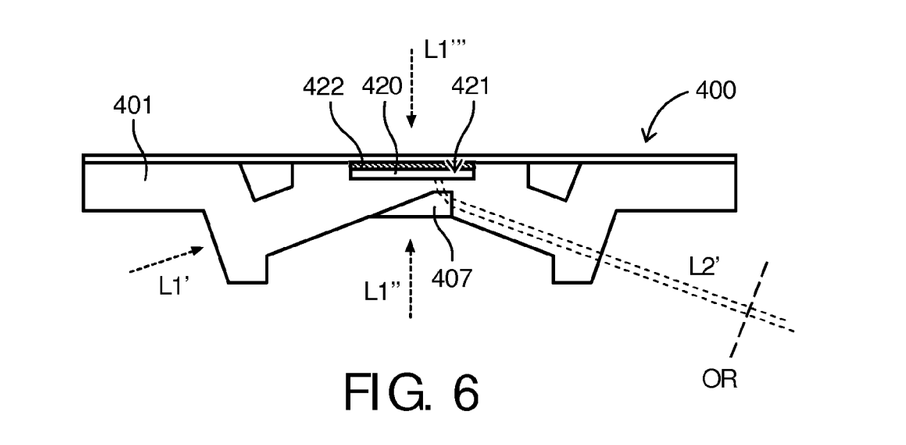
FIG. 6 shows a cross section through the inspectable chamber of a cartridge with a cavity for redirecting the second output light beam.

FIG. 6 shows a section through the inspectable chamber 420 of a fourth cartridge 400. The inspectable chamber 420 is similar in design to that of the previous embodiment (cartridge 300). Accordingly, a redirection of the second output light beam L2' is needed to enable that it reaches the observation region OR. This redirection is achieved by an optical element comprising a cavity or indentation 407 below the inspectable chamber 420. Besides this indentation 407, the remainder of the cartridge is the same as in the cross section of the TIR chamber (FIG. 2). The indentation 407 has the effect that the second output light beam L2' passes through this cavity and is twice refracted, i.e. when entering and leaving it. This redirects the second output light beam L2' appropriately such that it can leave the inspectable surface 421 under an angle smaller than the critical angle of TIR and simultaneously reach the observation region OR.

The Figure also shows that the inspectable chamber 420 can be illuminated with input light beams L1" or L1'" from the bottom or the top, respectively. Additionally, an input light beam L1' can be directed onto the inspection surface 421, if desired, under an angle of total internal reflection.

The described design has the advantage that a minor indentation 407 in the bottom of the cartridge 400 is sufficient to refract the light rays such that TIR on the cartridge-sample interface is avoided from the point of view of the detection branch. The shown indentation 407 is asymmetric to allow the explained different illumination options. This solution can be applied to individual detection chambers while it leaves the cartridge's exit windows intact.

Figure 7:
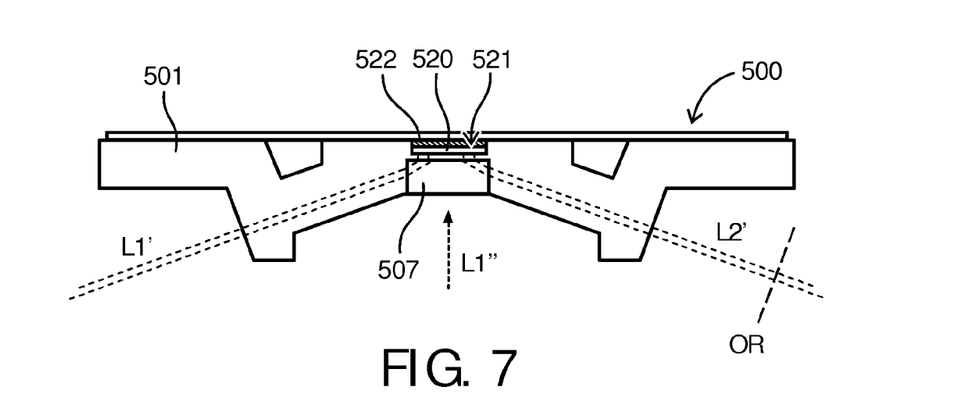
FIG. 7 shows a cross section through the inspectable chamber of a cartridge with a cavity for redirecting both the second output light beam and the corresponding input light beam.

FIG. 7 shows a section through the inspectable chamber 520 of a fifth cartridge 500. The difference with respect to the previous embodiment (cartridge 400) is that the cavity or indentation 507 below the inspectable chamber 520 is now symmetrical. An input light beam L1' directed towards the inspectable chamber 520 under an angle of total internal reflection will therefore be refracted in the same way as the second output light beam L2'. Accordingly, the light of such an input light beam L1' can enter the inspectable chamber 520.

Figure 8:
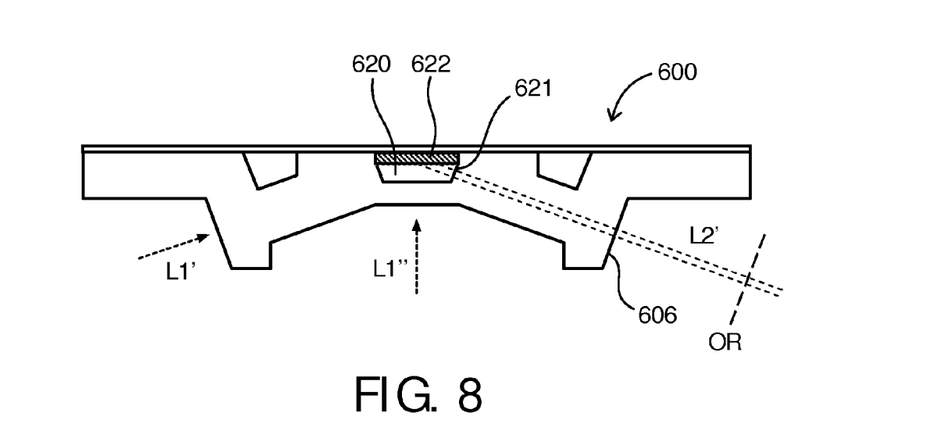
FIG. 8 shows a cross section through the inspectable chamber of a cartridge with a sample chamber exit window of modified inclination.

FIG. 8 shows a section through the inspectable chamber 620 of a sixth cartridge 600. The shape of this cross section is substantially identical to that of the cross section through the TIR chamber (FIG. 2), only the shape of the inspectable chamber 620 is different. In particular, the inspectable chamber 620 has an inspection surface 621, through which the second output light beam L2' leaves, that is no longer parallel to the detection surface of the TIR chamber (FIG. 2). Instead, the inspection surface 621 is inclined at an angle such that the second output light beam L2' can leave the inspectable chamber 620 (with or without refraction) towards the observation region OR. Preferably, the inspection surface 621 and the exit window 606 are parallel to each other and/or perpendicular to the second output light beam L2'.

Figure 9:
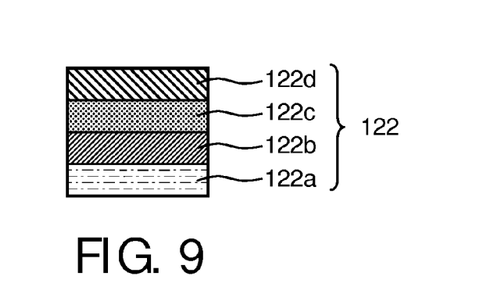
FIG. 9 shows a cross section through a typical reagent strip for colorimetric measurements.

FIG. 9 illustrates a typical embodiment of reagents that may be deposited in an inspectable chamber, for example the reagents 122 used in the inspectable chamber 120 of FIG. 3. These reagents 122 typically comprise a layered structure of, from bottom to top:

a foil 122*a*;
a color reagent 122*b*;
a transport paper 122*c* through which a liquid sample is transported by capillary forces;
a substrate 122*d* which serves as a mechanical carrier.

The strip 122 with reagents may be positioned upside down on the inspection surface 121 and illuminated with an input light beam L1'. The input light beam L1' reaches the color changing layer 122*b* of the strip 122 through the transparent top foil layer 122*a*, while the wetting of the color changing layer 122*b* takes place from the other side via the transport paper 122*c*.

This configuration is considered to be less suitable for integration of clinical chemistry in individual chambers of a multi-chamber cartridge together with immunoassays. Preferred embodiments of the invention therefore combine the color changing layer with for example the top foil of the cartridge (FIGS. 4-8). Transport paper is in these embodiments not required to establish contact with the sample fluid; the chambers are supposed to fill autonomously with sample fluid driven by capillary forces, just like the chambers in which the immunoassays take place.

In summary, the invention relates to a cartridge, a sensor device, and a method for the optical examination of a sample. A first output light beam L2 that originates from a total internal reflection at a detection surface 111 of a TIR chamber 121 and a second output light beam L2' that comes from the interior of an inspectable chamber 120-620 are both received within an observation region OR. Preferably, these output light beams are detected with the same light detector, e.g. an image sensor 12. The invention hence allows for observing a total internal reflection at the TIR chamber and for looking into the inspectable chamber from the same observation region OR. This is for example enabled by different inclinations of the windows encountered by the first and the second output light beams, by different optical elements in the paths of the output light beams, and/or by light scattering surface structures in the inspectable chamber. The invention can particularly be applied in combination with existing FTIR biosensors (e.g. Philips Magnotech platform).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A sensor apparatus for optical examination of a sample, comprising:
   a cartridge including a first sample chamber and a second sample chamber;
   at least one light source configured to irradiate the first sample chamber with a first input light beam and the second sample chamber with a second input light beam;
   wherein the first sample chamber and a direction of the first input light beam are configured such that the first input light beam is reflected from the first sample chamber by total internal reflection to form a first output light beam;
   wherein the second sample chamber is configured to reflect the second input light beam from an interior of the second sample chamber to form a second output light beam;
   a light detector configured to convert light received on a single image plane into an electrical signal for analysis by an analysis unit;
   at least one optical element configured to direct the first output light beam and the second output light beam to said single light detection surface such that the first output light beam and the second output light beam are detected with the same light detector.

2. The sensor apparatus according to claim 1, wherein the light detector includes a camera and the first and second output beams are received and mapped onto different regions of the image plane of the detector.

3. The sensor apparatus according to claim 1, wherein the first sample chamber and the second sample chamber are illuminated with input light beams that are parallel to each other.

4. A sensor apparatus for optical examination of a sample, comprising:
   a cartridge including a first sample chamber and a second sample chamber;
   at least one light source configured to irradiate the first sample chamber with a first input light beam and the second sample chamber with a second input light beam;
   wherein the first sample chamber and a direction of the first input light beam are configured such that the first input light beam is reflected from the first sample chamber by total internal reflection to form a first output light beam;
   wherein the second chamber includes a light scattering surface having color changing reagents adapted for detection of a range of analytes and is configured to reflect the second input light beam from an interior of the second sample chamber to form a second output light beam;
   a light detector configured to convert light received on a single image plane into an electrical signal for analysis by an analysis unit;
   at least one optical element configured to direct the first output light beam and the second output light beam to said single light detection surface such that the first output light beam and the second output light beam are detected with the same light detector.

5. The sensor apparatus according to claim 1, wherein the at least one light source is configured to direct the first and second input light beams along parallel paths to the first and second sample chambers, respectively.

6. The sensor apparatus according to claim 1, wherein first and second output light beams are non-parallel as they leave the first and second sample chambers and the optical element includes a prism structure which redirects one of the first and second output light beams relative to the other of the first and second output light beams.

* * * * *